United States Patent [19]

Gross

[11] 4,349,023
[45] Sep. 14, 1982

[54] EPIDURAL NEEDLE CATHETER AND ADAPTER

[75] Inventor: James R. Gross, Bartlett, Ill.

[73] Assignee: Abbott Laboratories, North Chicago, Ill.

[21] Appl. No.: 195,448

[22] Filed: Oct. 9, 1980

[51] Int. Cl.³ ............................................. A61M 25/00
[52] U.S. Cl. .................................. 128/214.4; 128/221; 128/DIG. 16
[58] Field of Search ...................... 128/214.4, 348, 349, 128/221, 6, DIG. 16

[56] References Cited

U.S. PATENT DOCUMENTS

| | | | |
|---|---|---|---|
| 2,009,825 | 7/1935 | Wappler | 128/349 R |
| 2,922,420 | 1/1960 | Cheng | 128/221 |
| 3,010,453 | 11/1961 | Doherty | 128/214.4 |
| 3,219,036 | 11/1965 | Stafford | 128/214.4 |
| 4,037,600 | 7/1977 | Poncy et al. | 128/214.4 |
| 4,235,232 | 11/1980 | Spaven et al. | 128/214.4 |

*Primary Examiner*—Dalton L. Truluck
*Attorney, Agent, or Firm*—Neil E. Hamilton; Robert L. Niblack

[57] ABSTRACT

A device which will permit the introduction of a length of catheter tubing through a needle and into the epidural space of a patient wherein the chance of the tubing being kinked is substantially reduced. In one version, an adapter having two opposing protruding sections is provided with one protrusion fitting inside the hub cavity of an epidural needle and the other extending outwardly to provide a finger engaging orifice surface. With one of the protruding sections placed in the needle hub cavity a continuous passageway is provided from the outwardly protruding section having the finger engaging surface and through the passageway of the adapter which will be aligned with the passageway in the epidural needle ultimately communicating with the needle. In an alternative embodiment, a protruding section extends from the hub of an epidural needle and a continuous passageway is provided therethrough to the needle as well as the protrusion providing a finger engaging surface so that the small diameter tubing can be easily fed therein.

11 Claims, 9 Drawing Figures

EPIDURAL NEEDLE CATHETER AND ADAPTER

BACKGROUND OF THE INVENTION

This invention relates to a device which will facilitate the introduction of catheter tubing through a needle. More particularly, it relates to an adapter or a needle structure which will facilitate the introduction of catheter tubing through an epidural needle and into the epidural space while substantially reducing the chances of the tubing becoming kinked.

In epidural anesthesia, a problem can arise in that once the epidural needle is placed in the epidural space it is necessary to feed a length of tubing into the space for proper positioning. In many instances, the tubing may engage tissue thus affording some resistance. Unless a continuous open passageway is provided for the cathetur tubing it will kink and not easily be moved to a desired position.

In U.S. Pat. No. 2,702,037 a hypodermic and coupling needle is illustrated which has two opposing and tapered conical coupling hubs which are dimensioned to fit within flexible tubing of standard proportions. In U.S. Pat. No. 3,782,381 an epidural catheter unit is disclosed which has a straightening member for precurved catheter tubing so as to permit the placement of the catheter tubing over an epidural needle without skiving of the catheter.

Nowhere in the prior art is there provided a means for introducing catheter tubing into an epidural needle so as to substantially reduce the risk of the tubing kinking as it is so introduced. U.S. Pat. No. 2,702,037 is not concerned with an epidural needle nor the introduction of catheter tubing through it. In U.S. Pat. No. 3,782,381 a multi-component assembly for epidural anesthesia is provided wherein a precurved length of epidural catheter tubing is first placed over an introducer needle. Subsequent to locating the catheter tubing in the epidural space, connection with the catheter tubing with an additional length of tubing must be effected.

It is an advantage of the present invention to afford a means of introducing a length of epidural catheter tubing into the epidural space in a quick and efficient manner. Other advantages are: a catheter adapter which can fit into the hub cavity of a standard epidural needle so as to afford a smooth passageway for the epidural tubing; a hub structure for an epidural needle which will facilitate the introduction of catheter tubing therethrough; a syringe adapter unit which will fit onto the epidural needle hub structure so as to provide fluid-tight communication with a hypodermic syringe during epidural needle puncture; and an epidural needle adapter or an epidural needle hub structure which can be produced at low cost and accordingly is disposable.

SUMMARY OF THE INVENTION

The foregoing advantages are accomplished and the shortcomings of the prior art are overcome by the present epidural needle adapter or epidural hub structure which will facilitate the introduction of catheter tubing into the epidural space. The adapter unit includes an intermediate body portion having a first protruding section extending from the intermediate body in a first direction and a second protruding section extending from the intermediate body in a second direction opposite the first. A continuous coaxial passageway extends through the intermediate body portion as well as the first and second protruding sections. The second protruding section has an entrane portion adjacent the passageway which is adapted to receive the catheter tubing. The first protruding section is constructed to be received with the hub cavity of the epidural needle and to provide coaxial alignment between the hub passageway and the first protruding section passageway. The second protruding section has a finger engaging surface surrounding the entrance portion. The finger engaging orifice has a reducing diameter portion adjacent the entrance and the intermediate body portion may include a collar member having an annularly spaced internal wall surface so as to afford frictional attachment means with the epidural needle hub.

In another embodiment, an epidural needle structure is provided which has an intermediate hub portion secured to the epidural needle and a protruding section extending from the epidural hub in the opposite direction. A passageway extends through the intermediate portion and the protruding section with the passageway disposed coaxially with respect to the passageway in the needle. The protruding section has an entrance portion adjacent the passageway which is adapted to receive the catheter tubing through the entrance portion. As is true with the adapter, the epidural needle hub structure also has a finger engaging surface surrounding the entrance portion so as to facilitate the feeding of the catheter tubing therethrough. With the epidural needle hub structure there is provided an adapter having two opposing internal compartments, one of the compartments having a wall surface with a taper substantially the same as the configuration of the protruding section and the other so as to provide fluid-tight engagement with a hypodermic syringe.

BRIEF DESCRIPTION OF DRAWING

A better understanding of the device for feeding catheter tubing through an epidural needle as provided in this invention will be afforded by reference to the drawing wherein.

DESCRIPTION OF ONE EMBODIMENT

Figure 1:
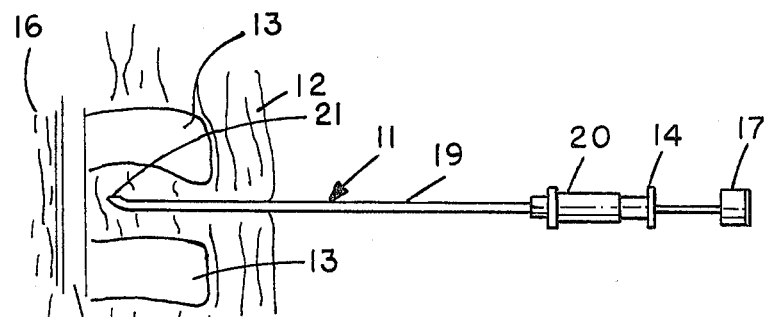
FIG. 1 is a view in side elevation showing a typical epidural puncture in a spine which is illustrated by a cross-section.
Figure 2:
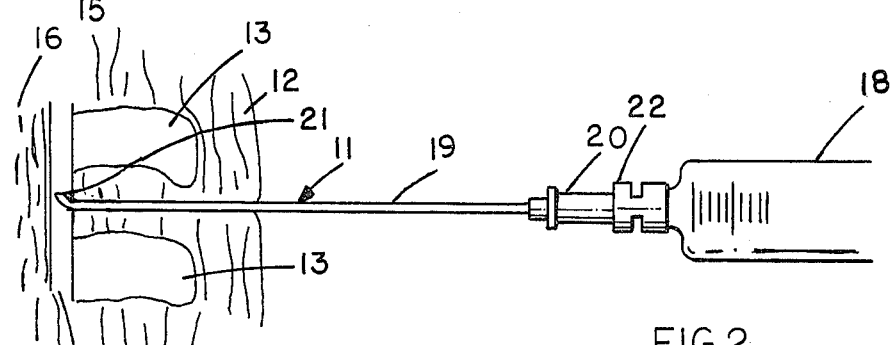
FIG. 2 is a view in side elevation of an epidural needle with a syringe attached and illustrating the standard loss of resistance procedure in locating the epidural needle into the epidural space.

Proceeding to a detailed description of one embodiment of the invention, which is shown in FIGS. 1–6, the catheter feeding device 10 will be utilized in conjunction with a standard epidural needle 11 having a needle portion 19 with an offset point 21 as well as a hub 20 with a flange 14. A stylet 17 is employed in conjunction with the epidural needle for purposes of preventing coring in the needle as the needle is pierced through the spinal ligaments 12 in order to place the point 21 in the epidural space 15 which is adjacent the spinal column 16. During the usual spinal column puncture which would take place between the vertebrae indicated by the numeral 13 the stylet will be employed in the needle until the needle is almost into the epidural space. The stylet is then removed and the standard loss of resistance technique is utilized which is illustrated in FIG. 2. This is effected by moving the piston of the syringe 18 inwardly until a slight resistance is detected. The epidural needle 11 is then moved inwardly slowly until the point 21 will enter the epidural space 15. This will be indicated by a drop of resistance in the syringe wherein the plunger will move inwardly. With the point 21 located in the epidural space 15, syringe 18 will be removed from flange 14 of hub 20 which previously engaged syringe connector 22.

Figure 3:
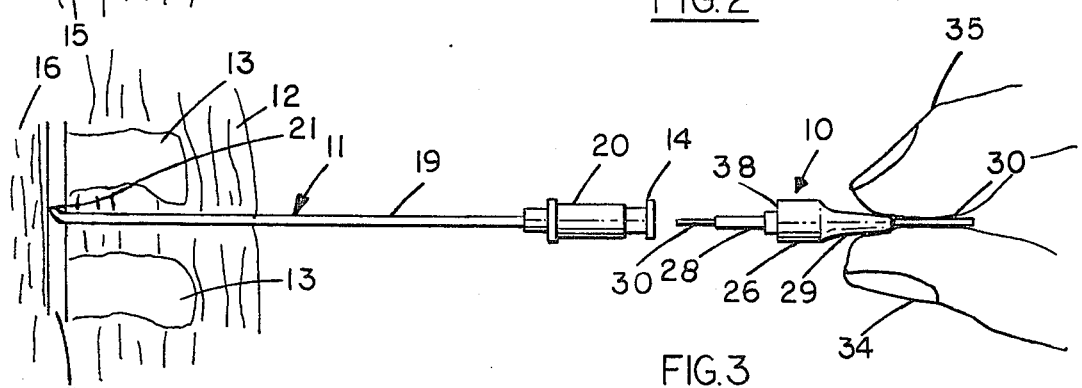
FIG. 3 is a view similar to FIG. 2 except with the syringe unit removed and the epidural tubing adapter of this invention being coaxially positioned for insertion into the epidural needle.
Figure 4:
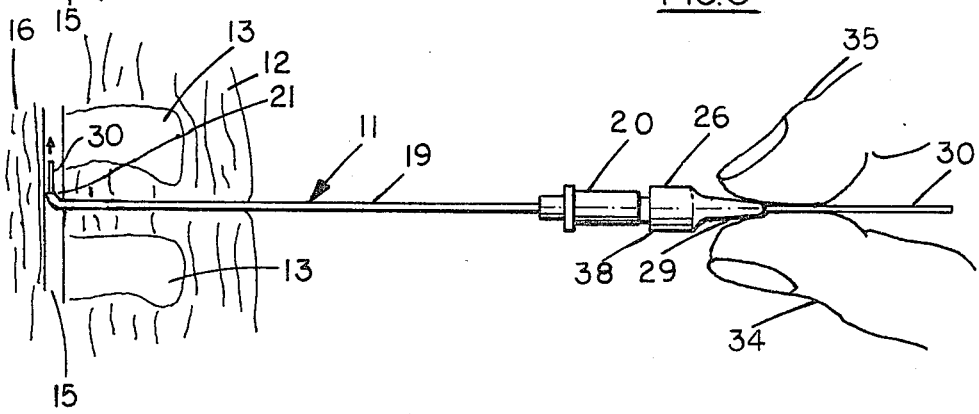
FIG. 4 is a view similar to the previous views except showing the epidural needle adapter frictionally engaged on the epidural needle hub.
Figure 5:
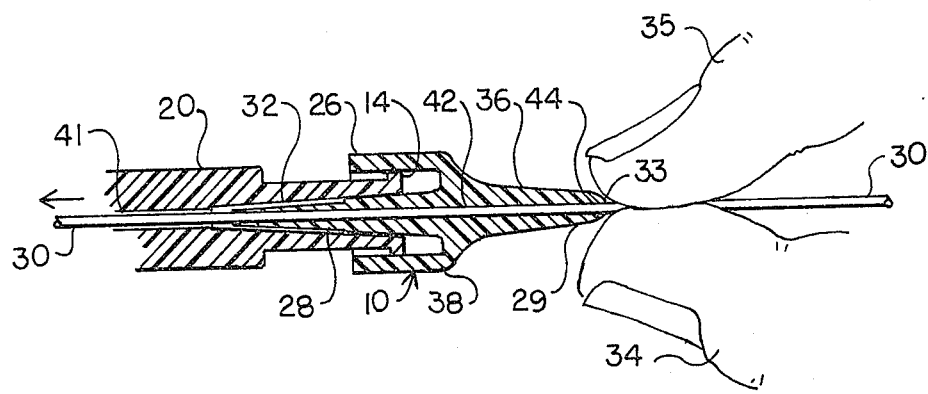
FIG. 5 is a view in vertical section of the epidural needle adapter engaging the epidural needle hub and further illustrating the movement of the fingers in feeding the epidural catheter tubing through the adapter and into the epidural needle.

At this stage it is necessary to feed a length of catheter tubing 30 into the epidural space 15 through the epidural needle 11. This is efficiently accomplished by means of the epidural feeding device 10 of this invention which is illustrated in FIG. 3. Catheter feeding device 10 includes a first protruding section 28 which is adapted to fit within epidural hub 20 and an opposite extending protruding section 29. Disposed between these two sections is an intermediate body portion 26 which includes a collar member 38 for engagement over flange 14. Referring to FIG. 4 it will be seen that a thumb 34 and finger 35 are shown feeding the catheter tubing 30 through the protruding section 29 through needle portion 19 and into the epidural space 15. The feeding of catheter tubing 30 is further illustrated in FIG. 5 wherein it will be noted that the first protruding section 28 has an external configuration substantially conforming to the Luer taper of the epidural needle hub cavity 32. As indicated in this FIGURE, a passageway 41 extends through the epidural needle hub 20 in communication with epidural needle portion 19. An additional passageway 42 is provided in catheter feeding device 10 and extends completely through entrance portion 44 of the second protruding section 29, the first protruding section 28 and intermediate body portion 26. This passageway 42 will have a diameter approximately the same as the outside diameter of tubing 30. It will be noted in this particular FIG. 5 that the first protruding section 28 substantially fills the epidural needle hub cavity 32 and that the epidural catheter feeding device 10 is further retained on hub 20 by means of collar member 38 having internal surface 39 for frictionally engaging flange 14.

Figure 6:
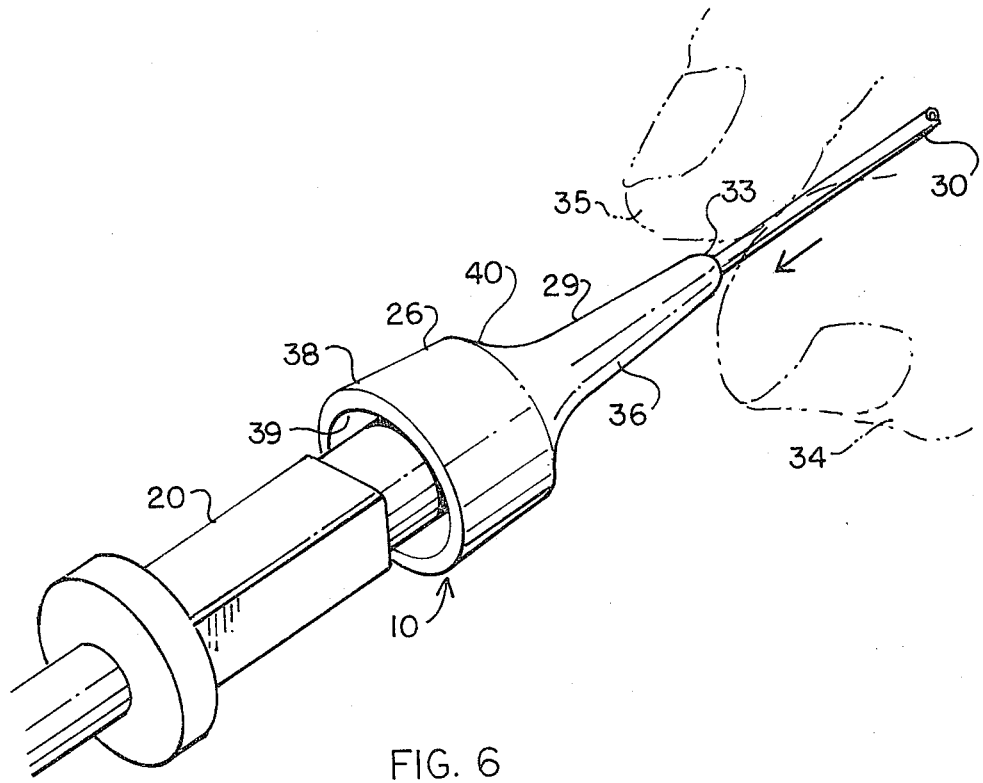
FIG. 6 is an enlarged view of the catheter feeding device illustrating the movement of fingers over the finger-engaging surface while feeding the catheter tubing into the adapter.

In FIG. 6, the motion of fingers 35 and 34 is best seen by an enlarged view of the catheter feeding device 10 as it is engaged on the epidural needle hub 20. It will be noted that the second protruding section 29 includes a tapered and conical surface 36 which terminates in a reduced diameter end which facilitates the movement of finger 35 and thumb 34 thereover. Conical surface 36 joins collar 26 in another reducing diameter portion 40.

DESCRIPTION OF AN ALTERNATIVE EMBODIMENT

Figure 7:
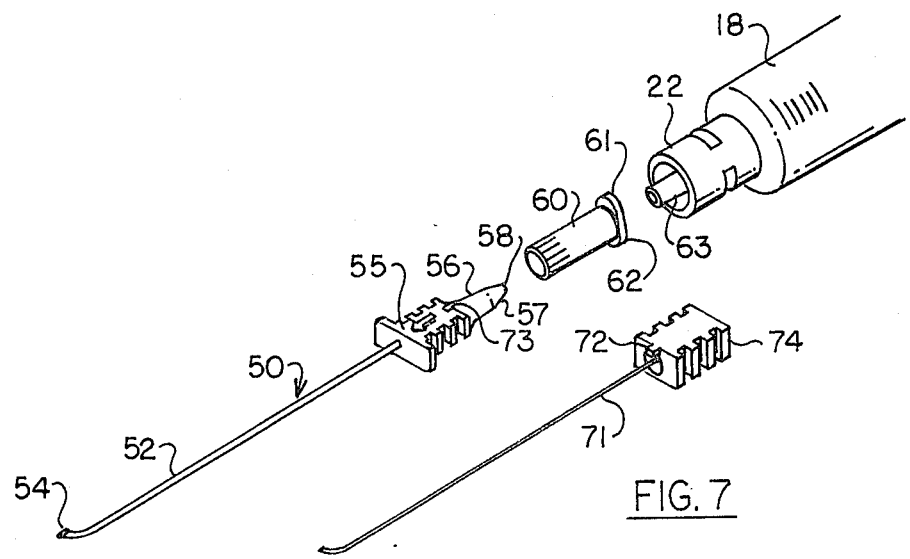
FIG. 7 is an assembly view of an alternate embodiment of this invention illustrating the epidural needle with a protruding hub portion, an adapter and a syringe for connection therewith.
Figure 8:
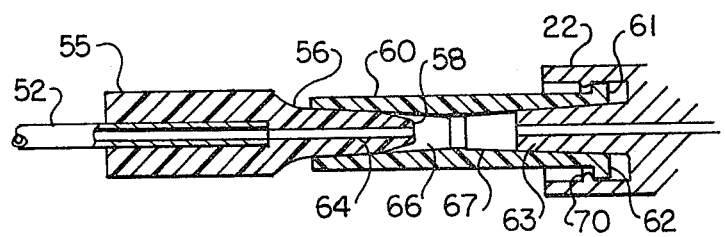
FIG. 8 is a view in vertical section illustrating the adapter shown in FIG. 7 in connection with the needle and the syringe.
Figure 9:
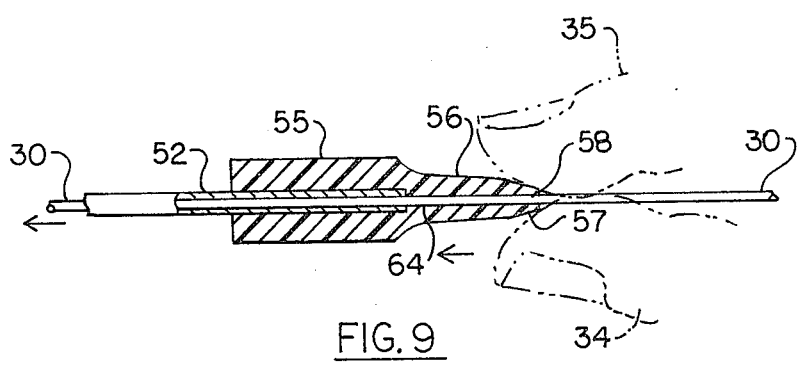
FIG. 9 is a view in vertical section illustrating the movement of the catheter tubing by the fingers through the needle illustrated in FIG. 7.

FIGS. 7–9 illustrate an alternative embodiment in that an epidural needle 50 is employed having the usual needle portion 52, hub 55 and offset point 54. A stylet 71 is provided having a hub 74 of generally the same geometric configuration as needle hub 55. For indexing purposes, projection 72 extends from hub 55 which is received in notch 73. In contrast to catheter feeding device 10, the intermediate hub portion 55 is constructed with a protruding section 56 with a finger engaging surface 57. The epidural needle 50 will be employed in the usual manner in epidural puncture as illustrated in FIGS. 1 and 2 in conjunction with the catheter feeding device 10. However, in order to permit the connection of syringe 18 for purposes of utilizing the loss of resistance technique during epidural puncture on adapter 60 is provided. Flanges 61 and 62 of adapter 60 will fit within syringe connector 22. As best illustrated in FIG. 8, adapter 60 is formed with one compartment 67 which will accommodate syringe nozzle 63 and a second compartment 66 which will accommodate protruding section 56. The flanges 61 and 62 of connector 60 will be frictionally held in the syringe connector 22 through the frictional engagement with ridge 70.

When it is desired to feed a length of catheter tubing 30 into the epidural space through the needle portion 52, connector 60 will be removed as will syringe 18 and a length of catheter tubing 30 will be fed in through protruding section 56. This is facilitated in that protruding section 56 is formed with a finger engaging surface 57 provided by a reducing diameter section 58. A passageway 64 extends through protruding section 56 as well as hub portion 55 communicating with the lumen of needle 52.

Operation

A better understanding of the advantages of catheter feeding device 10 and epidural needle 50 will be had by a description of their operation. The basic use of both of these devices has been previously explained. However, it will be appreciated that during the placement of flexible catheter tubing 30 into the epidural space 15 by means of epidural needles 11 or 50, there occurs in many instances, resistance to the tubing as it would be normally fed through the cavity of an epidural needle such as would be provided in needle hub 20. This is particularly illustrated by the numeral 32 in FIG. 5. If it were not for the first protruding section 28 filling the cavity 32 or the needle hub 55 having a passageway 64 extending therethrough the tubing 30 would kink therein when it is attempted to move the tubing into the epidural space. It will be appreciated that in many instances, although the needle point 21 or 54 is placed in the epidural space there may be tissue encountered causing a resistance to the end of the tubing as it is attempted to be forced through the needle. Further, the movement of the tubing in through the epidural needle is also facilitated by means of the contour of the second protruding sections 29 and 56. An important feature of the invention is in having a finger engaging surface 33 or 57 in the form of a reducing diameter section. This effects movement of the thumb and finger over the tubing and onto the respective, conical, protruding sections in a stable manner with the guidance of the catheter tubing through the catheter feeding device 10 or the needle unit 50.

After the tubing 30 is properly placed in epidural space 15, epidural needles 11 and 30 will be removed by retracting the needles back over the tubing. To facilitate connection with a syringe an adapter such as the locking cannula mount described in U.S. Pat. No. 4,006,744 will be attached and the unit taped to the body.

It will be noted in comparison between device 10 and needle 50 that a double taper or discontinuous surface is utilized as represented by conical surface 56 and reducing diameter section 58 in conjunction with hub 55 while a continuous tapering conical surface 36 is utilized in second protruding section 29 of unit 10. This is due to the fact that a Luer taper (2+36') is preferred for protruding section 56 to effect a fluid tight connection with syringe 18 as is accomplished through adapter 60 and compartment 66. As to the reducing diameter portion 58 an angle of 15° is preferred. However, this angle can range from 2° to 20° and still be effective. Referring to unit 10, a connection with syringe 18 is not required. Accordingly, one continuous surface 36 can be employed having an angle preferably of 5°. However, this can vary from 2° to 15°.

Catheter feeding device 10 as well as epidural needle 50 are disposable. Catheter feeding device 10 with the protruding sections 28 and 29 are preferably formed of a polypropylene plastic material. However, other materials such as polystyrene or rubber could be employed. Similarly, the hub portion 55 and the protruding section 56 of epidural needle 50 is formed of a polypropylene material while other matrial such as polystyrene could be substituted. The preferred method of making these parts is the injection molding process.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:

1. For use with an epidural needle having a needle and hub portion with a cavity in the hub portion and a passageway extending between said cavity and said needle, a device for feeding catheter tubing through said epidural needle into the epidural space while substantially reducing the risk of kinking of the tubing, said device comprising:
   an intermediate body portion;
   a first protruding section extending from said intermediate body portion in a first direction;
   a second protruding section extending from said intermediate body portion in a second direction opposite said first direction;
   a continuous, coaxial passageway extending through said intermediate body portion and said first and second protruding sections, said passageway having a diameter approximately the same as the outside diameter of said tubing;
   said second protruding section defining an entrance portion adjacent said passageway, said passageway adapted to receive said catheter tubing through said entrance portion in said second protruding section;
   said first protruding section constructed and arranged to be received within said hub portion cavity and to provide coaxial alignment between said hub passageway and said first protruding section passageway;
   said second protruding section defining a finger engaging orifice surface surrounding said entrance portion and defined by a substantially conical configuration with the smallest diameter portion located adjacent said entrance portion to said passageway;
   so that when said first protruding section is inserted into said hub cavity a length of catheter tubing can be easily fed through said epidural needle and into the epidural space.

2. The device for feeding catheter tubing as defined in claim 1 wherein said finger engaging surface has a reducing taper in the range of 2 to 15°.

3. The device for feeding catheter tubing as defined in claim 1, wherein said intermediate body portion includes a collar member having an annularly spaced internal wall surface, said needle hub and the internal spaced wall defining an attachment means.

4. The device for feeding catheter tubing as defined in claim 3 wherein said attachment means is defined by flange members extending from said epidural needle hub and an internal, frictional surface disposed in said wall of said collar member.

5. The device for feeding catheter tubing as defined in claim 2 wherein said intermediate body portion includes a collar member and said second protruding section and said collar member are joined by a reducing diameter portion.

6. In an epidural needle having a needle portion with an offset point, an intermediate hub portion secured to said epidural needle and a passageway extending through said needle and hub portions adapted to receive a length of catheter tubing, the improvement comprising:
   a protruding section extending from said intermediate hub portion in a direction opposite said needle;
   a passageway extending through said protruding section and disposed coaxially with respect to said passageway in said hub and needle portions;
   said protruding section defining an entrance portion adjacent said passageway therein;
   said passageway in said protruding section having a diameter approximately the same as the outside diameter of said catheter tubing and adapted to receive said catheter tubing through said entrance portion;
   said protruding section defining a finger engaging surface surrounding said entrance portion and having a substantially conical configuration with the smallest diameter portion located adjacent said entrance portion;
   so that a length of catheter tubing can be easily fed through said protruding section of said epidural needle and into the epidural space while substantially reducing kinking of the tubing in the hub portion.

7. The improved epidural needle structure as defined in claim 6 wherein said finger engaging surface includes a reducing diameter portion adjacent said entrance portion with the smallest diameter positioned at the passageway entrance.

8. The improved epidural needle structure as defined in claim 7 wherein said conical configuration has a taper of 2° and said reducing diameter portion has a taper of 2° to 20°.

9. In an epidural needle assembly having a needle portion with an offset point, an intermediate hub portion secured to said epidural needle and a passageway extending through said needle and hub portions adapted to receive a length of catheter tubing, the improvement comprising:

a protruding section extending from said intermediate hub portion in a direction opposite said needle;

a passageway extending through said protruding section and disposed coaxially with respect to said passageway in said hub and needle portions;

said protruding section defining an entrance portion adjacent said passageway therein;

said passageway in said protruding section having a diameter approximately the same as the outside diameter of said catheter tubing and adapted to receive said catheter tubing through said entrance portion;

said protruding section defining a finger engaging surface surrounding said entrance portion and having a substantially tapering conical configuration with the smallest diameter portion located adjacent said entrance portion; and an adapter member defining two oppositely disposed internal compartments, said one of said compartments having a wall surface with a taper complementary to said tapering conical configuration;

so that fluid communication can first be made through the other of said compartments and subsequently a length of catheter tubing can be easily fed through said protruding section of said epidural needle and into the tubing in the hub portion.

10. The improved epidural needle assembly as defined in claim 9 wherein said other compartment is constructed and arranged to receive a nozzle portion of a hypodermic syringe.

11. The improved epidural needle assembly as defined in claim 10 further including frictional engagement means extending from said adapter member adjacent said other compartment for engagement with said hypodermic syringe.

* * * * *